United States Patent [19]

della Valle et al.

[11] Patent Number: 4,940,694

[45] Date of Patent: Jul. 10, 1990

[54] THERAPEUTIC USE OF GM1 IN SEVERE CEREBRAL ISCHEMIC STROKES PATHOLOGIES

[75] Inventors: Francesco della Valle, Padova; Aurelio Romeo, Rome; Silvana Lorenzi, Padova, all of Italy

[73] Assignee: Fidia, S.p.A., Abano Terme, Italy

[21] Appl. No.: 338,516

[22] Filed: Oct. 20, 1988

Related U.S. Application Data

[63] Continuation of Ser. No. 127,603, Nov. 30, 1987, abandoned, which is a continuation of Ser. No. 734,105, May 15, 1985, abandoned.

[30] Foreign Application Priority Data

Feb. 18, 1985 [IT] Italy .................. 47698 A/85

[51] Int. Cl.$^5$ .............................. A61K 31/70
[52] U.S. Cl. ........................ 514/25; 514/54; 536/53; 536/55.1
[58] Field of Search .............. 536/53, 55.1; 514/54, 514/25

[56] References Cited

U.S. PATENT DOCUMENTS

| 4,415,733 | 11/1983 | Tayot | 536/55.1 |
| 4,435,389 | 3/1984 | Mutai et al. | 514/54 |
| 4,476,119 | 10/1984 | Valle et al. | 514/25 |
| 4,521,593 | 6/1985 | Martin | 536/53 |
| 4,631,294 | 12/1986 | Barsan | 514/557 |

FOREIGN PATENT DOCUMENTS 0072722 2/1983 European Pat. Off. ........... 536/17.9

OTHER PUBLICATIONS

Maladies et Medicaments/Drugs and Diseases 1984, vol. 1, No. 3, 44-53, Borzeix.
Journal of Neuroscience Research 12:493-498 (1984), S. Bassi et al.
Clinical Neuropharmacology, vol. 7, Suppl. 1, 1984, M. Reivich et al.
Gangliosides and Neuronal Plasticity, Fidia Research Series, vol. 6, Liviana Press, Padova (1986), pp. 435-443, Cahn et al.
Journal of Neuroscience Research 12:397-408 (1984), Toffano et al.
Cerebrovascular Diseases, 1981, F. Plum.
Eur. Neurol. 24:343-351 (1985), Battistin et al.
Neurology, vol. 22, Apr. 1972, pp. 377-383, Patten et al.
Nature, vol. 323, 9 Oct. 1986, Sabel et al.
Science, vol. 225, pp. 340-341.
Dev. Neurosci. 6:73-100 (1983/84), Varon et al.
Prog. Clin. Biol. Res. 79 (1982), Varon et al.
Minerva Medica, 66, 3774-3784 (1985), Lipparini et al.
Journal of Neuroscience Research 7:363-370 (1982), Domanska-Janik et al.
Chemical Abstracts 89:213206w, Mirzoyan et al.
Chemical Abstracts 89:1066a, Sekoyan.
Adv. Exp. Med. Biol. 174, 593-600 (1984), Horowitz.

Primary Examiner—Ronald W. Griffin
Attorney, Agent, or Firm—Birch, Stewart, Kolasch & Birch

[57] ABSTRACT

A pharmaceutical preparation containing the ganglioside $GM_1$ or an inner ester derivative thereof and a method for increasing cerebral blood flow in stroke victims by acute administration of $GM_1$ or its inner ester derivative.

5 Claims, No Drawings

THERAPEUTIC USE OF GM1 IN SEVERE CEREBRAL ISCHEMIC STROKES PATHOLOGIES

This application is a continuation of application Ser. No. 127,603 filed Nov. 30, 1987, now abandoned, which is a continuation of Ser. No. 734,105, filed May 15, 1985, now abandoned.

BACKGROUND AND FIELD OF THE INVENTION

Gangliosides are complex glycolipid molecules which are natural components of cellular membranes and have a structure containing a carbohydrate portion to which is linked a ceramide and sialic acid moiety. The carbohydrate portion includes at least one galactose or glucose moiety and at least one N-acetylglucosamine or N-acetylgalactosamine moiety. The general structure of a ganglioside can then be represented by the following formula:

one mole of a sialic acid {one mole of ceramide; at least one mole of galactose or glucose; at least one mole of N-acetylglucosamine or N-acetylgalactosamine} where all of the moieties are linked by a glucosidic bond.

Numerous gangliosides have been identified and have been found to be particularly abundant in nerve tissue, especially in brain tissue. Various studies have shown that the most important of the sialic acids found in gangliosides are N-acetyl-neuraminic acid (NANA) and, to a lesser degree, N-glycolylneuraminic acid. Of the numerous gangliosides which have been identified, the following gangliosides, labeled by their international symbols, have been found to exist in significant amounts in ganglioside mixtures extracted from bovine brain tissue:

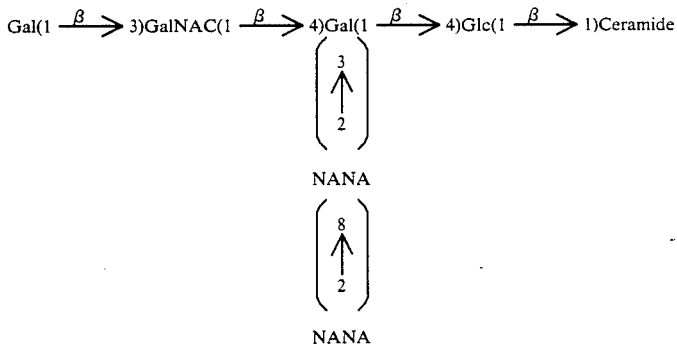

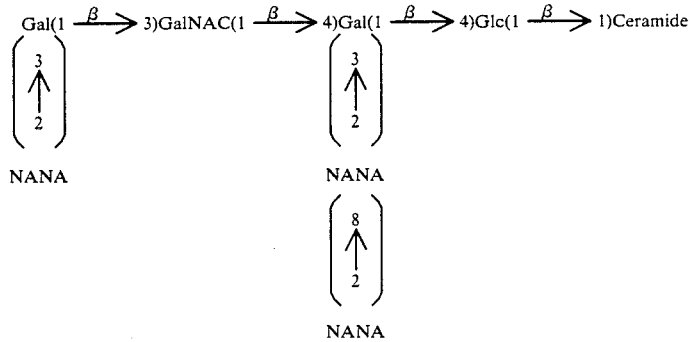

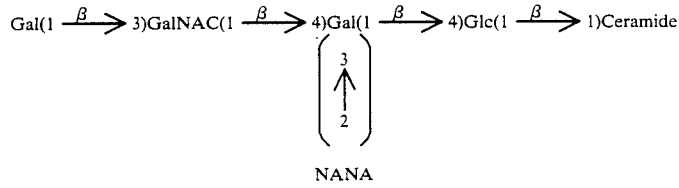

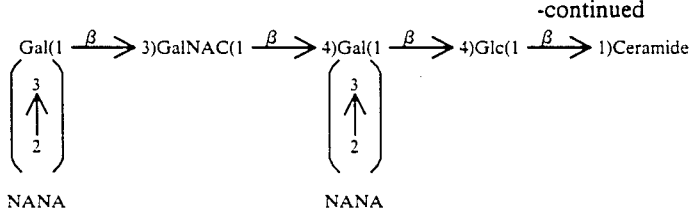

where Glc represents glucose, GalNAC represents N-acetylgalactosamine, Gal represents galactose, NANA represents N-acetyl-neuraminic acid and the percentages in parenthesis indicate the amount of each ganglioside found in the ganglioside mixture extracted from bovine brain tissue.

Since gangliosides are mainly associated with neuronal membranes, it has been suggested that they may play a role in the transfer of information across these membranes (Fishmann P. H., Brady R. O. (1976): Science, 194, 906-915). Such a role is now envisaged in the recognition and interaction phenomena that underlie the differentiation, maturation and synaptic contacting of neuronal circuitry. In particular one ganglioside, $GM_1$ (monsialoganglioside), has been implicated in neuronal differentiation processes in mouse cerebellum (Willinger M., Schachner M. (1980). Dev. Biol., 74, 101-107) and in neurite induction in cortical neurons in cats (Purpura D. P., Baker H. J/ (1977). Brain Res. 143, 13-26).

A specific role for ganglioside $GM_1$ in facilitating the formation of synaptic contacts was suggested by experiments which found that $GM_1$-enrichment would facilitate the formation of neuromuscular junctions in nerve-muscle cocultures (Obata K. and Handa S. (1979). In "Integrative Control Functions of the Brain". Ed.Ito et al., 2, 5-14). A distinct pharmacological effect of the administration of exogenous gangliosides (a bovine brain extraction product) was defined by Gorio et al. (Gorio A., Carmignoto G., Facci L., Finesso M. (1980), Brain Res., 197, 236-241) as a reinnervation-stimulating activity due to enhanced nerve sprouting, resulting in early functional recovery after traumatic peripheral nerve damage. This pharmacological action was found to be operative also in the central nervous system (CNS) and reports have described the accelerated recovery of cholinergic enzyme activity in the rat hippocampus after extensive electrocoagulative septal lesions, when the animals were treated intramuscularly with exogenous gangliosides (Woicik M. Ulas J., Oderfeld-Nowak B. (1982). Neuroscience, 7, (2), 495-499). This accelerated recovery of cholinergic biochemical parameters in the hippocampus was assumed to reflect reinnervation of the hippocampus through enhanced neuronal sprouting and regrowth of new cholinergic nerve terminals originating from the intact part of the septum.

The nerve sprouting phenomenon is a physiological response of intact neurons deprived of their normal synaptic contacts. The sprouting response appears to represent the repair mechanism by way of which a functional restoration may be achieved after damage to neuronal circuitry. A considerable body of evidence on the occurrence and the functional significance of such repair mechanisms has accumulated (Bjorklund A., Stenevi U. (1979). Physiological Reviews, 59, (1), 62-100 and Cottman C. W., Nieto-Sampedro M., Harris E. (1981). Physiological Reviews, 61, (3), 684-784). With the progress of understanding of these mechanisms, the concept of "CNS-neuroplasticity" was born, as opposed to the long-standing dogma of inability of the adult CNS to initiate repair sequences after injury.

The monosialogaglioside $GM_1$ is an experimental drug being developed on the hypothesis, confirmed in experimental models, that the exogenous administration of this ganglioside should favorably influence CNS neuroplasticity, promote regeneration in the CNS and thus enhance functional recovery after brain and spinal cord lesions.

Unilateral hemitransection in rats has been used to assess the effects of exogenous $GM_1$ administration in situations of traumatic CNS damage. The recovery of nigrostriatal dopaminergic parameters after unilateral hemitransection has favorably influenced $GM_1$ treatment (Toffano et al. (1983a). Brain Res. 261, 165-166, Savoini et al., (1982). Comparison of the time course of changes in tyrosine hydroxylase (TH) activity in the lesioned striatum of animals treated with 30 mg/kg $GM_1$ i.p., to that of rats treated with saline shows a marked influence of $GM_1$ treatment on the recovery of TH activity. In rats treated with $GM_1$ a significant increase of Vmax for TH was observed on day 14 which persisted until the end of the observation, i.e., 76 days. The effect of $GM_1$ was dose-dependent. A significant increase of TH-related immunofluorescence and homovanillic acid (HVA) content was determined in the striatum ipsilateral to the lesion in rats treated with $GM_1$. In the $GM_1$-treated group the sensitivity to apomorphine (turning behaviour) was significantly reduced in comparison to the saline-treated group. The increase of TH activity, HVA content, TH-related immunofluorescence detected in the striatum ipsilateral to the lesion and the decreased sensitivity of lesioned rats to apomorphine after $GM_1$ treatment, are compatible with the interpretation that a functional dopaminergic reinnervation of the striatum is facilitated by $GM_1$ treatment after hemitransection. These results indicate that $GM_1$ treatment in a model of traumatic CNS damage causes an improvement of biochemical, morphological and functional markers of nigrostriatal dopaminergic pathways. These effects are apparent only on the lesioned side (for 14 days after hemitransection), while no changes are detected in the unlesioned side of the operated animals.

Further data in this model described that $GM_1$ treatment partially prevented the decrease of TH activity caused by hemitransection in the substantia nigra ipsilateral to the lesion. Concomitantly a significant increase of TH-immunoreactivity in both the striatum and the substantia nigra was detected. In particular, chronic treatment with $GM_1$ increased the TH-positive nerve terminals in the striatum, prevented the disappearance of TH-positive cell bodies in the substantia nigra and induced the appearance of longer TH-positive neurites with respect to control treatment (physiological saline). These data lend further support to the presumed action of $GM_1$ ganglioside in this model: facilitation of dopaminergic reinnervation of the striatum and preservation of vital dopaminergic cell bodies in the substantia nigra. This pharmacological intervention thus enhances the efficacy of restorative neuroplasticity.

This investigation was carried a step further by including receptor density analysis in the evaluation of the effects of chronic $GM_1$ treatment (10 mg/kg i.p. once daily for 56 days) on the degenerative and regenerative features of nigrostriatal dopamine (DA) neurons following hemitransection in rats (L. F. Agnati et al., Acta Physiol. Scand. suppl. 532, 37–42, 1984). Nigral DA cell bodies with their dendrites and the striatal DA nerve terminals were demonstrated by tyrosine hydroxylase immunocytochemistry. Morphometrical analysis of DA cell bodies, dendrites and terminals were performed in each animal. In addition, the relative contents of tyrosine hydroxylase was evaluated as optical density. The distribution of the DA receptors in the striatum was evaluated by means of quantitative receptor autoradiography using as radioligands the DA receptor antagonist $^3$H-spiperone and the DA receptor agonist $^3$H-N-propylnorapomorphine ($^3$H-NPA). Chronic $GM_1$ treatment resulted in the maintenance of the number of DA cell bodies in the substantia nigra on the lesioned side and also increased dendrite length of the DA nerve cells in the zone reticulata on that side. Moreover, this treatment maintained the density of striatal DA terminals on the lesioned side and possibly also the number of striatal nerve cells onto which DA nerve fibers project. Furthermore, the lesion induced DA receptor supersensitivity was counteracted by chronic treatment with $GM_1$. The hypothesis was introduced that following ganglioside treatment lesioned DA nerve cells do not degenerate, but elongate their dendrites to give increased trophic support to DA cell bodies with intact DA axons. These increased dendrodendritic interactions may enable the unlesioned DA cells to increase the density of their striatal nerve terminal networks via collateral sprouting.

Favourable biochemical evidence of a pharmacological effect of exogenous $GM_1$ was also obtained in a different model of traumatic CNS damage. Reports have described the effects of i.m. treatment with $GM_1$ ganglioside on the recovery of cholinergic innervation of the hippocampus after electrocoagulative lesion, in the septum of rats, monitoring the enzymatic activities linked with ACh metabolism (Oderfeld-Nowak et al. (1982). Report for WHO Study Group on Neuroplasticity and Repair in CNS.Geneva (CH), Jun. 28–Jul. 2). Also, effects on metabolism of endogenous $GM_1$ were studied in this model. Chronic administration of $GM_1$ significantly facilitated recovery of the enzyme activities, indicative for cholinergic innervation. Septal lesions caused a decrease of hippocampal $GM_1$ levels in untreated animals.

Specific biochemical evidence of $GM_1$ pharmacological action on CNS level was obtained wherein the in vivo modulation of serotonin receptors in rat dorsal cerebral cortex by subchronic treatment with $GM_1$ (Agnati et al. (1983b) (Acta Physiol. Scand. 117, 311–363) (10 mg/kg i.p. daily for 3 days) was demonstrated by means of $^3$H-spiperone-binding in membrane preparations from treated rats. $^3$H-spiperone labeled serotonin receptors in the dorsal cerebral cortex were modulated by $GM_1$ treatment, without any modulation of $^3$H-spiperone-labeled DA receptors in the striatum.

Evidence has also shown the degeneration-preventing and/or regrowth-stimulating activity in noradrenergic and serotonergic neurons damaged by selective neurotoxins in the neonatal stage of cerebral development. The neurotoxic treatment caused a marked and permanent degeneration of distal noradrenergic and serotonergic nerve terminal projections in the brain, associated with permanent chemical sympathectomy. When $GM_1$ was administered (30 mg/kg s.c. for 4 days after neurotoxic treatment of neonates), the treated animals showed, one month later, marked improvements over controls in serotonergic markers in the cortex. Also moderate counteracting effects were noted on chemically induced sympathectomy.

Behavioral correlates of recovery from bilateral caudate nucleus damage in rats have also been reported. The preliminary results obtained in this study indicate that i.p. treatment with $GM_1$ (30 mg/kg daily for 14 days) significantly improved the learning of a cognitive task after surgical damage to the caudate nuclei.

However, in all these tests, the pharmacological effect of $GM_1$ was obtained after chronic or subchronic treatment.

These data give no evidence or suggestion of an acute effect of $GM_1$.

The present inventors, however, studying the effect of $GM_1$ in an experimental model of stroke, have surprisingly discovered very impressive findings of an acute effect. These findings may have a very significant clinical relevance and are described below.

OBJECTS AND SUMMARY OF THE INVENTION

It is therefore, one object of the present invention to provide a method for the acute treatment of stroke victims by administering the ganglioside $GM_1$.

It is another object of the invention to provide a pharmaceutical composition containing the ganglioside $GM_1$ adapted for administration to stroke victims for acute treatment.

It is a further object of the invention to provide a method for the acute treatment of stroke victims, and a composition adapted for the method, whereby the ganglioside $GM_1$ is administered to stroke victims to increase cerebral blood flow in an ischemic brain without altering arterial blood pressure.

These and other objects of the present invention are accomplished by providing a method for administering the ganglioside $GM_1$ or its inner ester derivative and a pharmaceutical composition containing the compounds adapted for such use, to stroke victims for acute treatment after the stroke, whereby cerebral blood flow is advantageously increased without unfavorably affecting arterial blood pressure.

DETAILED DESCRIPTION OF THE INVENTION

The active substances in the composition of the invention are the sodium salt of ganglioside $GM_1$, one of the major gangliosides present in mammalian nerve tissue, and its derivative inner ester. The term ganglioside is an accepted trivial group name for sialic acid-containing glycosphingolipids. These complex glycolipids are acidic, water-soluble and not dialyzable. The ganglioside molecule is amphipathic, consisting of a lipophilic moiety comprising sphingosine and fatty acids, in particular stearic acid, and a hydrophilic oligosaccharide moiety. Ganglioside $GM_1$ is a monosialoganglioside (the ganglioside family is differentiated by the varying number and position of sialic acid residues present in the molecule). Monosialoganglioside $GM_1$ may be considered a basic compound in the ganglioside series, since metabolic manipulation of more complex gangliosides will invariably lead to ganglioside $GM_1$. Svennerholm (Svennerholm L. (1963 . J. Neurochem., 19, 613–623) proposed a classification system and nomenclature, which has entered into common use. Other denominations are:

Monosialotetrahexosylganglioside, sodium salt $II^3$-alpha-N-acetylneuraminosyl-gangliotetraglycosyl ceramide sodium salt (IUPAC-IUB name)

$II^3$-alpha-NeuAc-GgOse$_4$Cer, sodium salt (IUPAXI-UB abbreviation)

Chemical Abstract Registry Number: RN (37758-47-7).

The symbol $GM_1$ conforms to the Svennerholm system. More complex abbreviatory names were devised by the IUPAC-IUB Lipid Document (1977).

Extraction and purification procedure

The monosialoganglioside is a biological substance obtained from bovine brain with the following structural formula:

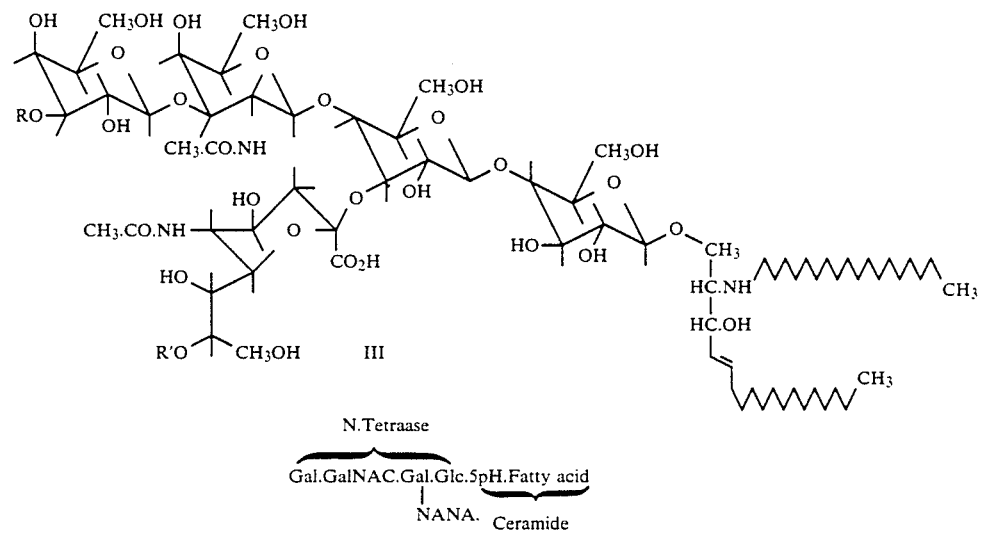

$G_{M1}$: R = R' = H $II^3$-alpha-NeuAc-GgOse$_4$Cer

The sodium salt of monosialotetrahexosylganglioside $GM_1$ can be isolated as a highly purified product according to the procedure described by Tettamanti et al. (Biochimica et Biophysica Acta, 296 (1973) 160–170) or obtained from Fidia S.p.A., Abano Terme, Italy. Starting from frozen cattle brains a multistep separation procedure, based on solvent extraction, liquid/liquid partitioning, phospholipid removal by methanolysis, and molecular filtration yields a highly purified ganglioside mixture (itself used as active ingredient in injectable preparations), which contains ganglioside $GM_1$ in a percentage between about 18 and 24% in comparison to a reference working standard with known structure and purity. This compound is separated from the mixture by a two-step High Performance Liquid Chromatography procedure, giving a final yield of approximately 75% of the theoretical value. The obtained substance is converted to the sodium salt, dialized and precipitated. The precipitate is redissolved in water, submitted to sterilizing filtration and lyophilized. The purity of the compound obtained is more than 98% referring to dry weight by photodensitometry assay, in comparison to a reference working standard with known structure and purity.

The compound obtained after this purification has the following chemical characteristics and specifications:

Molecular weight 1,574 (Calculated on the basis of the presence of 1 mole of NANA, 1 mole of glucose, 2 moles of galactose, 1 mole of galactosamine, sphingosine 18:1, stearic acid and sodium salt).

Appearance

Odourless, hygroscopic, white-cream powder.

Solubility

Soluble in water, methanol-water and methanol-chloroform. Virtually insoluble in methanol, acetone, chloroform, ether and hexane.

Melting point

207°–230° C.

Specifications

| | |
|---|---|
| Identity | positive in three tests (structural analysis by gas chromatography for the singular components, I.R. spectrum, TLC in 2 different solvents, identity of sodium) |
| pH (1% w/v) | 7.5–8.5 |
| Loss on drying | less than 0.3% |
| Impurities (TLC) | less than 2.0% |
| Residual solvents | less than 0.2% |

Example of pharmaceutical preparations

For the purposes of the present invention the ganglioside $GM_1$, preferably a pharmaceutically acceptable salt thereof, especially the sodium salt, is prepared as a pharmaceutical composition in admixture with one or more pharmaceutically acceptable excipients, carriers or diluents. The ganglioside $GM_1$ can be utilized as a drug in pharmaceutical preparations administered to humans or animals intramuscularly, subcutaneously or intradermally, by intravenous injection or infusion. The preparations can be solutions of the compound or a lyophilized powder of the compound in association with one or more pharmaceutically acceptable carriers or diluents, and contained in buffered media at a suitable pH and isotonic with physiological fluids. The dosage administered will depend upon the desired effect and upon the desired administration route.

The following, although not limitative of the invention, are specific exemplary preparations containing the ganglioside $GM_1$.

EXAMPLE 1:

| One vial is composed as follows: | |
|---|---|
| Sodium salt of monosialotetrahexosyl-ganglioside $GM_1$ | 20.0 mg. |
| Dibasic sodium phosphate.$12H_2O$ | 6.0 mg. |
| Monobasic sodium phosphate.$2H_2O$ | 0.5 mg. |
| Sodium chloride | 16.0 mg. |
| Water for injection, q.s. ad | 2.0 ml. |

EXAMPLE 2:

| One vial is composed as follows: | |
|---|---|
| Sodium salt of monosialotetrahexosyl-ganglioside $GM_1$ | 40.0 mg. |
| Dibasic sodium phosphate.$12H_2O$ | 6.0 mg. |
| Monobasic sodium phosphate.$2H_2O$ | 0.5 mg. |
| Sodium chloride | 16.0 mg. |
| Water for injection, q.s. ad | 2.0 ml. |

EXAMPLE 3:

| One vial is composed as follows: | |
|---|---|
| Sodium salt of monosialotetrahexosyl-ganglioside $GM_1$ | 100.0 mg. |
| Dibasic sodium phosphate $12H_2O$ | 15.0 mg. |
| Monobasic sodium phosphate $2H_2O$ | 1.25 mg. |
| Sodium chloride | 40.0 mg. |
| Water for injection, q.s. ad | 5.0 mg. |

It is also considered by the present inventors that the inner-ester derivative of $GM_1$ would have activity in administration to stroke victims to increase cerebral blood flow in an ischemic brain without altering arterial blood pressure. The inner ester derivatives are described, for example, in U.S. Pat. No. 4,476,119 and EPO patent application No. 072,722, published Feb. 23, 1983.

The inner esters of gangliosides are formed by the reaction between the carboxyl group of a sialic acid moiety with a hydroxyl group of one of the carbohydrate moieties or another adjoining sialic acid within the same ganglioside molecule. The formation of the inner ester bond, together with the normal glucosidic bond between the sialic acid and carbohydrate moiety creates a lactonic ring, typically five or six-membered, characteristic of the structure of the inner ester ganglioside derivatives. Various inner ester derivatives can be formed depending upon the particular bonding but the inner ester derivatives are generally formed of a carbohydrate portion, at least one ceramide and at least one sialic acid moiety wherein one or more of the sialic acids are ester bonded to a carbohydrate moiety and/or one or more of the sialic acids are ester bonded to an adjoining sialic acid. The preferred derivatives are those which are fully lactonized, that is, wherein each sialic acid is ester bonded to the carboxyl group of a carbohydrate moiety or to the hydroxy group of an adjoining sialic acid.

With particular relevance to the present invention, the inner ester derivative of the $GM_1$ ganglioside can be prepared according to the procedures described, for example, in U.S. Pat. No. 4,476,119 and EPO published application No. 0072722, noted above.

For exemplary purposes, the following procedures can be utilized to prepare an inner ester derivative of $GM_1$.

EXAMPLE 4

8 g of $GM_1$ (sodium salt) are dissolved in 80 ml of distilled water and passed through a column filled with 10 g of Dowex 50 w×8 (100–200 mesh triethylammonium form).

This product, anhydrified in high vacuum, is dissolved (with the aid of a sonicator bath) in 200 ml of anhydrous tetrahydrofuran containing 4 ml of triethylamine.

This solution is slowly added to 600 ml of anhydrous tetrahydrofuran (4 hours) containing 20 mM of 2-chloro-1-methyl-pyridinium salt (where the anion could be, for example, iodide, toluene-4-sulfonate, trifluoromethane sulfonate, etc.), under continuous stirring and maintaining a constant temperature of 45° C.

This reaction is carried out for 18 hours at 45° C.

The excess reagent is filtered off and the mixture is concentrated in a stream of nitrogen, the residue is redissolved in 80 ml of chloroform/methanol 1/1 and precipitated in 400 ml of acetone. The product is finally dried in high vacuum.

Yield - 7.0 g (88,4% of the theoretical value).

Thin layer chromatograph: On silica gel plates, solvent system chloroform/methanol/$CaCl_2$0.3% (55/45/10), the $R_f$ of the final product (0.70) exceeds the $R_f$ (0.65) of the starting compound. The chromatograph results thus show the absence of any starting material. By treatment with 0.1N solution of $Na_2CO_3$ at 60° C. for one hour, the ester bond is cleaved and the original ganglioside can be obtained.

The IR spectrum of the inner ester of $GM_1$, performed on a KBr pellet, shows the typical ester absorption of 1750 $cm^{-1}$.

EXAMPLE 5

8 g of $GM_1$ (sodium salt) are dissolved in 80 ml of distilled water and passed through a column filled with 10 g of Dowex 50 w×8 (100–200 mesh pyridinium form).

This product, anhydrified in high vacuum, is dissolved in 800 ml of anhydrous tetrahydrofuran and 2.1 g (30 mM) of ethoxyacetylene.

This mixture is refluxed for 3 hours, the refluxer is cooled at −10° C. and equipped with an anhydrifying valve.

After removing the solvents and excess of ethoxyacetylene, the residue is dissolved in 80 ml of chloroform/methanol 1/1 and precipitated in 400 ml of acetone.

Yield - 7.2 g (91.0% of the theoretical value).

Thin layer chromatography: On silica gel plates, solvent system chloroform/methanol/CaCl$_2$ 0.03% (55/45/10), the R$_f$ of the final product (0.70) exceeds the R$_f$ (0.65) of the starting compound. The chromatography results thus show the absence of any starting material. By treatment with 0.1N solution of Na$_2$CO$_3$ at 60° C. for one hour, the ester bond is cleaved and the original ganglioside can be obtained.

The IR spectrum of the inner ester of GM$_1$ performed on a KBr pellet, shows the typical ester absorption of 1750 cm$^{-1}$.

EXAMPLE 6

8 g of GM$_1$ (sodium salt) are dissolved in 80 ml of distilled water and passed through a column filled with 10 g of Dowex 50 w×8 (100–200 mesh pyridinium form).

This product, anhydrified in high vacuum and dissolved in 200 ml of anhydrous pyridine, is added to a suspension of 1.26 g (5 mM) of the Zwitterionic Woodward reagent (N-ethyl-5-phenyl-isoxazolium-3'-sulfonate), in 200 ml of anhydrous pyridine. This reaction mixture is stirred for 10 days at room temperature.

After filtration of the excess reagent and complete removal of the solvent, the residue is dissolved in 80 ml of chloroform/methanol 1/1 and precipitated in 400 ml of acetone.

Yield - 6.3 g (79.5% of the theoretical value).

Thin layer chromatograph: On silica gel plates, solvent system chloroform/methanol/CaCl$_2$ 0.3% (55/45/10), the R$_f$ of the final product (0.70) exceeds the R$_f$ (0.65) of the starting compound. The chromatography results thus show the absence of any starting material. By treatment with 0.1N solution of Na$_2$CO$_3$ at 60° C. for one hour, the ester bond is cleaved and the original ganglioside can be obtained.

The IR spectrum of the inner ester of GM$_1$ performed on a KBr pellet, shows the typical ester absorption of 1750 cm$^{-1}$.

Similar to the preparations described above for the ganglioside GM$_1$ the following are examples of pharmaceutical preparations containing the inner ester derivative of the ganglioside GM$_1$.

| Preparation No. 1 | |
|---|---|
| One lyophilized ampoule contains: | 20.0 mg |
| inner ester of GM$_1$ derivative | |
| One buffer ampoule contains: | |
| dibasic sodium phosphate.12H$_2$O | 6.0 mg |
| monobasic sodium phosphate.2H$_2$O | 0.5 mg |
| sodium chloride | 16.0 mg |
| water for injection, q.s. ad | 2.0 ml |
| Preparation No. 2 | |
| One lyophilized ampoule contains: | 100.0 mg |
| inner ester of GM$_1$ derivative | |
| One buffer ampoule contains: | |
| dibasic sodium phosphate.12H$_2$O | 15.0 mg |
| monobasic sodium phosphate.2H$_2$O | 1.25 mg |
| sodium chloride | 40.0 mg |
| water for injection, q.s. ad | 5.0 ml |

Biological activity in short term test:

The following biological test and data therefrom show the utility of the administration of GM$_1$ to stroke victims. Male cats having induced regional cerebral ischemia were utilized as the test model.

Test on the cerebral blood flow in an experimental stroke.

The experiments were carried out on 13 male cats (weighing 2.5–3.5 kg.) anaesthetized with 40 mg/kg pentobarbitol sodium. Briefly, regional cerebral ischemia was induced by occluding the proximal portion of the left middle cerebral artery (MCA) by a miniature Mayfield clip. After 2 hours of MCA occlusion, the clip was removed, and the blood flow through the MCA was reinstated. Eight out of 13 occluded animals were treated with ganglioside GM$_1$ (30 mg/kg) and inner ester derivative of GM$_1$(5 mg/kg) intravenously when the MCA occlusion was released.

Reflected light of cerebrocortical NADH fluorescence and reflectance, measured at 366 nm, was used according to Eke et al. (Am. J. Physiol 236, 759–768, 1979) to determine the changes in cerebrocortical vascular volume (CVV), mean transit time cortical blood flow (t$_m$), and cerebral blood flow (CBF). The reflectance base line, measured at the beginning of the experiments during the control period, was regarded as representing 100% CVV. In order to determine the reference value of t$_m$, 0.1–0.3 ml isosmotic and oxygenated dextran solution was injected into the lingual artery. Mean transit time was calculated from the hemodilution-induced reflectance reactions by the area over height analysis (Maier and Zierler, (1954) J. Appl. Physiol. 6, 731–744). The reference value of t$_m$ was regarded as 100%. In order to determine 0% CVV, the blood was washed out from the brain via the lingual artery. The difference in cortical reflectance obtained between the blood perfused (100% Cvv) and blood-free (0% CVV) brain was linearly divided to calculate CVV changes. Finally, CBF changes were calculated by dividing the percentage values of CVV with the percentage values of t$_m$ (Maier and Zierler: J. Appl. Physiol. (1954); 6 731–744, Eke et al., 1979). Concomitantly arterial blood pressure was recorded from the femoral artery. The parameters were recorded on an eight-channel Hewlett-Packard polygraph.

TABLE 1

Effect of GM$_1$ treatment 30 mg/kg i.v. and GM$_1$ inner ester 5 gm/kg i.v. on the kinetics of CBF recovery, and on arterial blood pressure after ischemic damage from moderate to severe ischemic insult caused by an occlusion of 120 minutes of the MCAO.

| Groups | Control CBF % | Occ. 120 Min. CBF % | Ril. 2 Min CBF % | Ril. 60 Min CBF % | Ril. 120 Min CBR % | Ril. 180 Min CBF % | Ril. 240 Min CBF % |
|---|---|---|---|---|---|---|---|
| | | | Untreated | | | | |
| X n.5 | 100 | 16.4 | 106.1 | 77.6 | 78.1 | 84.3 | 91.6 |
| ± S.E. | 0 | 4.6 | 28.4 | 13.1 | 7.7 | 12 | 9.7 |
| | | | Treated with GM$_1$ | | | | |
| X n.5 | 100 | 23.1 | 171.2 | 185.2 | 151.0 | 190.6 | 198.2 |
| ± S.E. | 0 | 6.8 | 31.4 | 31.8 | 19.0 | 6.9 | 12.3 |
| | | | Treated with GM$_1$ inner ester | | | | |
| X n.4 | 100 | 29.8 | 170.5 | 188.3 | 182.5 | 178.3 | 185.6 |

TABLE 1-continued

Effect of GM$_1$ treatment 30 mg/kg i.v. and GM$_1$ inner ester 5 gm/kg i.v. on the kinetics of CBF recovery, and on arterial blood pressure after ischemic damage from moderate to severe ischemic insult caused by an occlusion of 120 minutes of the MCAO.

| Groups | Control CBF % | Occ. 120 Min. CBF % | Ril. 2 Min CBF % | Ril. 60 Min CBF % | Ril. 120 Min CBR % | Ril. 180 Min CBF % | Ril. 240 Min CBF % |
|---|---|---|---|---|---|---|---|
| S.E. | 0 | 4,2 | 32,6 | 36,9 | 28,2 | 35,5 | 31,2 |

Compounds were administered i.v. when the occlusion of the MCAO was open. The average arterial blood pressure was not meaningful different between these groups.
When the compounds were injected, the average arterial blood pressure in the untreated group was of 150 ± 7,3 mm Hg, 160 ± 3,2 Hg in the animals treated with GM$_1$, 148 ± 6,2 in the group of animals treated with GM$_1$ inner ester.

TABLE 2 ges in the different physiological parameters during the occlusion of the MCAO after its opening

| | Controls | | | | | Treated Group with GM$_1$ | | | | | Group treated with inner ester GM$_1$ ganglioside | | | | |
|---|---|---|---|---|---|---|---|---|---|---|---|---|---|---|---|
| | C | 0-60 | R-60 | R-120 | R-180 | C | 0-60 | R-60 | R-120 | R-180 | C | 0-60 | R-60 | R-120 | R-180 |
| MABP mm Hg | 132,0 4,6 | 153 8,3 | 147,5 5,8 | 147,5 5,8 | 147,5 5,8 | 133,0 5,1 | 146 9,1 | 168,0 7,4 | 159,0 10,3 | 166,0 6,8 | 146,2 6,2 | 150 4,1 | 165,7 5,0 | 147,5 2,5 | 162,3 3,5 |
| ICP mm Hg | 4,5 0.6 | 5,0 0,5 | 5,4 0,8 | 5,4 0,8 | 5,2 0,7 | 4,9 0,6 | 5,4 0,8 | 9,5 2,2 | 10,0 2,0 | 11,5 2,2 | 5,0 0,7 | 4,5 0,8 | 5,0 0,5 | 5,5 0,5 | 5,0 0,8 |

Results are described as average ± standard error ±; n shows the average number of experiments.
C = control period; 0-60 = occlusion 60 minutes;
R-60, R-120, R-180 = 60, 120 and 180 minutes after opening of the occlusion.
MABP = main arterial blood pressure;
ICP = intracranial pressure.

Results

Occlusion of the middle cerebral artery led to similar changes in cerebrocortical vascular volume, mean transit time of cortical blood flow and cortical blood flow in stroke groups. CBF at the end of MCAO was 16.4 ±4.6%, 23.1 ±6.8% and 29.8 ±4.2% of its preischemic reference value in the "untreated" and "treated" with GM$_1$ and inner ester GM$_1$ derivative stroke groups respectively. At 60 minutes following the release of MCAO, significant CBF increase occurred in the GM$_1$ and inner ester derivative treated stroke groups, and CBF was slightly smaller than its preischemic reference value in the untreated stroke group. In other words, the treatment GM$_1$ and the inner ester of GM$_1$ significantly improved CBF without alteration of arterial blood pressure (see Tables 1 and 2). During the later phases of recovery, CBF remained approximately at the same high level in the stroke group treated with GM$_1$ and the GM$_1$ inner ester, while in the untreated stroke group, it slowly recovered close to its preischemic reference level.

From the results it is clear that 120 minutes MCAO (middle cerebral artery occlusion) resulted in a similar degree of pronounced ischemia in both experimental stroke groups as indicated by changes in CBF. Upon recirculation, CBF in the untreated stroke group showed slight and short-lived reactive hyperemia, but marked and extended reactive hyperemia in the stroke groups treated with GM$_1$ or the inner ester.

Conclusion and Therapeutic Applications

When evaluating the importance of the discovery as a whole, it should be borne in mind that this acute effect, demonstrated for GM$_1$ and its inner ester derivative, proves to be complementary to the chronic effect observed in models of regeneration of the CNS previously described, and represents an advantage in that it improves the metabolic supply of the cells in the area damaged by the ischemic attack.

Indeed, the finding that the ganglioside GM$_1$ and its inner ester derivative is able to increase CBF in a previously ischemic brain without altering arterial blood pressure may have significant clinical relevance. Whereas previous investigations have only reported chronic effects for long term administration of the compounds, it has now surprisingly been found by the present inventors that administration of GM$_1$ or its inner ester derivative to stroke victims provides an important acute therapeutic effect by increasing cerebral blood flow. This utility for GM$_1$ and the inner ester derivative thereof clearly has clinical relevance to the recovery and cerebral damage control of stroke victims.

As discussed above, the discovery of the present invention relates to the acute effect of GM$_1$ and its inner ester derivative for increasing CBF. This acute effect is particularly realized by the administration of GM$_1$ or its inner ester derivative within 10 days, preferably within 7 days, after the occurrence of a stroke. GM$_1$ or its inner ester derivative are most preferably administered within one or two days after a stroke. In this manner, the most effective utility of GM$_1$ or its inner ester derivative is realized by increasing metabolic supply to the brain cells, thereby preventing neuronal death.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for the treatment of cerebral stroke patients which comprises administering to said patients an effective amount of the ganglioside GM$_1$, or a pharmaceutically acceptable salt of said ganglioside GM$_1$.

2. A method for increasing cerebral blood flow and preventing neuronal death, which comprises administering an effective amount of the ganglioside GM$_1$, or a pharmaceutically acceptable salt thereof to patients in need of such treatment.

3. A method for increasing cerebral blood flow in stroke patients and preventing neuronal death, without undesirably altering arterial blood pressure which comprises administering to said patients an effective amount of the ganglioside $GM_1$, or a pharmaceutically acceptable salt thereof.

4. A method according to claim 1, wherein said ganglioside $GM_1$ is administered to said patient within seven days after the occurrence of a stroke.

5. A method according to claim 1, wherein said ganglioside $GM_1$ is administered to said patient within two days after the occurrence of a stroke.